United States Patent [19]

Vlattas

[11] Patent Number: 4,507,311
[45] Date of Patent: Mar. 26, 1985

[54] IMIDAZO[1,2-c][1,3]BENZODIAZEPINES

[75] Inventor: Isidoros Vlattas, Summit, N.J.

[73] Assignee: Ciba-Geigy Corporation, Ardsley, N.Y.

[21] Appl. No.: 602,649

[22] Filed: Apr. 23, 1984

Related U.S. Application Data

[60] Division of Ser. No. 444,957, Nov. 29, 1982, Pat. No. 4,460,587, which is a continuation-in-part of Ser. No. 328,274, Dec. 7, 1981, abandoned.

[51] Int. Cl.³ .................. A61K 31/415; C07D 487/04
[52] U.S. Cl. ..................... 260/239 BD; 260/239 BC; 260/243.3; 260/245.6
[58] Field of Search .............. 260/239 BC, 239 BD, 260/245.6, 243.3; 424/273 R

[56] References Cited

U.S. PATENT DOCUMENTS

| | | | |
|---|---|---|---|
| 3,539,573 | 11/1970 | Schmutz | 544/359 |
| 3,838,122 | 4/1974 | Sah et al. | 260/247.5 B |
| 3,933,794 | 1/1976 | Hester, Jr. et al. | 260/245.6 |
| 4,192,803 | 3/1980 | Wright, Jr. et al. | 260/243.3 |
| 4,280,957 | 7/1981 | Walser et al. | 260/244.4 |
| 4,337,198 | 6/1982 | Sorg et al. | 260/243.3 |
| 4,444,688 | 4/1984 | Vlattas | 260/245.6 |

FOREIGN PATENT DOCUMENTS 2077727 12/1981 United Kingdom .

OTHER PUBLICATIONS

Wright, Jr. et al., J. Med. Chem., 1980, 23, 462-465.

Primary Examiner—Donald G. Daus
Assistant Examiner—Cecilia Shen
Attorney, Agent, or Firm—Norbert Gruenfeld

[57] ABSTRACT

5-Diazacycloalkylimidazo[1,2-c][1,3]benzodiazepines, for example compounds of the formula

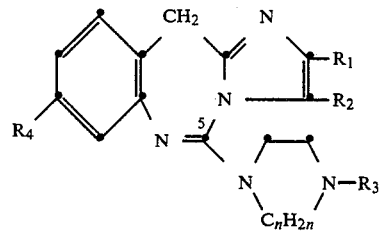

in which e.g., $R_1$, $R_2$ and $R_4$ are hydrogen, $R_3$ is methyl and $C_nH_{2n}$ is $CH_2CH_2$, have neuroleptic and/or antihistaminic activity. The synthesis, pharmaceutical compositions and methods of treatment utilizing such compounds are described.

2 Claims, No Drawings

IMIDAZO[1,2-c][1,3]BENZODIAZEPINES

This is a divisional of application Ser. No. 444,957 filed Nov. 29, 1982, now U.S. Pat. No. 4,460,587, which is a continuation-in-part of application Ser. No. 328,274 filed Dec. 7, 1981, now abandoned.

BACKGROUND OF THE INVENTION

Piperazinyl substituted ring fused benzodiazepines have been reported as antipsychotic/neuroleptic agents, e.g., clozapine (U.S. Pat. No. 3,539,573) and 11-piperazinyl-5H-pyrrolo[2,1-c][1,4]benzodiazepines (U.S. Pat. No. 4,192,803). On the basis of available literature, the 11H-imidazo[1,2-c][1,3]benzadiazepine ring system has not been described in the art.

SUMMARY OF THE INVENTION

The present invention concerns and has for its object the novel 5-diazacycloalkyl-imidazo[1,2-c][1,3]benzodiazepines and derivatives thereof. The invention also relates to processes for preparing said compounds, pharmaceutical compositions comprising said compounds, and application of said products in the treatment or management of psychoses (e.g. aggression, agitation) and/or allergy, when administered, alone or in combination, to mammals.

The compounds of formula I exhibit valuable pharmacological properties, e.g. antihistaminic and psychotherapeutic, e.g. antipsychotic (neuroleptic) effects. Said compounds, being essentially free of extrapyramidal effects, represent a novel chemical class of useful tranquilizers, primarily neuroleptic agents, essentially devoid of side effects e.g. dyskinesia and catalepsy seen with the classical major tranquilizers.

DETAILED DISCLOSURE OF THE INVENTION

Particularly the invention relates to compounds of formula I

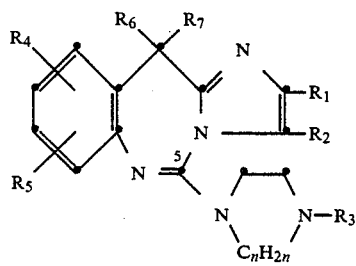

wherein $R_1$ and $R_2$ are independently hydrogen, lower alkyl, lower alkanoyl, halogen, cyano, carboxy, lower alkoxycarbonyl, carbamoyl, sulfamoyl, mono- or di-lower alkyl-(carbamoyl or sulfamoyl); $C_nH_{2n}$ is lower alkylene separating both nitrogen atoms by 2 or 3 carbon atoms; $R_3$ is hydrogen, lower alkyl, lower alkenyl, lower alkynyl, lower alkanoyl, aryl lower alkyl, lower alkoxycarbonyl, phenyl-loweralkoxycarbonyl, or (hydroxy, lower alkanoyloxy, aryloxy or lower alkoxy) lower alkyl having at least two carbon atoms; $R_4$ and $R_5$ independently represent hydrogen, lower alkyl, lower alkoxy, lower alkylthio, halogen, trifluoromethyl, hydroxy, lower alkanoyloxy, sulfamoyl, mono- or di-lower alkylsulfamoyl; and $R_6$ and $R_7$ represent hydrogen or lower alkyl; the N-oxides, lower alkyl quaternary derivatives and salts, especially pharmaceutically acceptable salts thereof.

Preferred embodiments of this invention relate to compounds of formula I wherein each of $R_1$ and $R_2$ is hydrogen, lower alkyl, cyano, carboxy, lower alkoxycarbonyl or carbamoyl; n represents the integer 2 to 4; $R_3$ is hydrogen, lower alkyl, lower alkoxycarbonyl, or hydroxy lower alkyl of 2 to 4 carbon atoms; $R_4$ represents hydrogen, lower alkyl, lower alkoxy, lower alkylthio, halogen or trifluoromethyl; $R_5$ represents hydrogen; and $R_6$ and $R_7$ represent hydrogen or lower alkyl; the N-oxides; lower alkyl quaternary salts; or pharmaceutically acceptable salts thereof.

Highly preferred are compounds of formula I wherein each of $R_1$ and $R_2$ is hydrogen, methyl, ethyl, cyano, carboxy, alkoxycarbonyl of 1 to 3 carbon atoms in the alkoxy portion or carbamoyl; n represents the integer 2 or 3; $R_3$ is hydrogen, alkyl of 1 to 3 carbon atoms, alkoxycarbonyl of 1 to 3 carbon atoms in the alkoxy portion, hydroxyethyl or hydroxypropyl; $R_4$ represents hydrogen, methyl, methoxy, methylthio, chloro or trifluoromethyl; $R_5$ represents hydrogen; $R_6$ and $R_7$ represent hydrogen or methyl; the N-oxides; methyl quaternary salts; and pharmaceutically acceptable salts thereof.

Especially useful are compounds of formula II

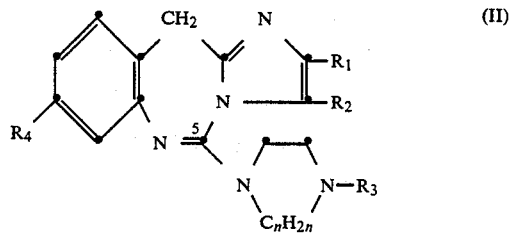

wherein $R_1$ and $R_2$ independently represent hydrogen or lower alkyl; $R_3$ represents hydrogen, lower alkyl or hydroxy lower alkyl wherein the hydroxy group is separated from the nitrogen atom by at least 2 carbon atoms; $R_4$ represents hydrogen, lower alkyl, lower alkoxy, lower alkylthio, halogen or trifluoromethyl; $C_nH_{2n}$ represents ethylene or propylene; the N-oxides; and pharmaceutically acceptable salts thereof.

Of particular interest are compounds of formula II wherein $R_1$ and $R_2$ independently represent hydrogen or methyl; $R_3$ represents hydrogen, methyl, ethyl, propyl, 2-hydroxyethyl or 3-hydroxypropyl; $R_4$ is hydrogen, methyl, methoxy, fluoro, chloro or trifluoromethyl; $C_nH_{2n}$ represents ethylene or propylene; the N-oxides and pharmaceutically acceptable salts thereof.

The said compounds of formula II wherein $C_nH_{2n}$ represents ethylene are preferred.

Further preferred are compounds of formula II wherein $R_1$ and $R_2$ independently represent hydrogen or lower alkyl; $R_3$ represents hydrogen, lower alkyl, or hydroxy lower alkyl wherein the hydroxy group is separated from the nitrogen atom by 2 carbon atoms; $R_4$ represents hydrogen, lower alkyl, halogen or trifluoromethyl; and $C_nH_{2n}$ represents ethylene; the N-oxides; and pharmaceutically acceptable salts thereof.

Particularly preferred are compounds of formula II wherein $R_1$ and $R_2$ independently represent hydrogen or methyl; $R_3$ represents hydrogen, methyl, ethyl, propyl or 2-hydroxyethyl; $R_4$ is hydrogen, methyl, fluoro, chloro or trifluoromethyl; and $C_nH_{2n}$ represents ethylene; and pharmaceutically acceptable acid addition salts thereof.

The general definitions used herein have the meanings within the scope of the present invention as follows.

The term "lower" referred to above and hereinafter in connection with organic radicals or compounds respectively defines e.g. such alkyl, alkenyl and alkynyl radicals with up to and including 7, preferably up and including 4 and advantageously one or two carbon atoms.

Halogen is preferably fluoro or chloro, but may also be bromo or iodo.

A lower alkyl group or such present in said alkoxy, alkylthio or other alkylated groups, is above all methyl, but also ethyl, n- or i-(propyl, butyl, pentyl, hexyl or heptyl), e.g. 2-methylpropyl or 3-methylbutyl; lower alkenyl is preferably allyl; lower alkynyl is preferably propargyl.

Aryl lower alkyl is preferably benzyl, 1-, 2- or 3-phenylpropyl, 1- or 2-phenylethyl, said radicals being optionally substituted on the phenyl ring preferably by e.g. halogen, lower alkoxy or lower alkyl.

A lower alkoxy group preferably contains 1 to 4 carbon atoms and represents for example ethoxy, propoxy, isopropoxy or advantageously methoxy.

A lower alkylthio group preferably contains 1 to 4 carbon atoms and represents for example ethylthio, propylthio or advantageously methylthio.

The term "acyl" represents for example lower alkanoyl, lower alkoxy-carbonyl, carbamoyl, sulfamoyl, mono- or di-lower alkyl (carbamoyl or sulfamoyl), halosulfonyl, phenyl-lower-alkoxycarbonyl and the like.

Lower alkanoyl is preferably acetyl or propionyl. Lower alkanoyloxy is preferably acetyloxy or propionyloxy.

A lower alkoxycarbonyl, mono- or di-lower alkyl(carbamoyl or sulfamoyl) group is preferably ethoxycarbonyl, methoxycarbonyl; mono- or dimethyl(carbamoyl or sulfamoyl).

A phenyl-lower alkoxycarbonyl group represents preferably benzyloxycarbonyl.

A lower alkylene group $C_nH_{2n}$ is especially ethylene; but also 1,2- or 1,3-propylene, 1,2-, 1,3- or 2,3-butylene; thus forming with both adjacent nitrogen atoms a piperazinyl or homopiperazinyl moiety.

A lower hydroxyalkyl group is preferably 2-hydroxy-(ethyl or propyl), 3-hydroxy-(propyl or butyl) or 4-hydroxybutyl.

A lower alkanoyloxy lower alkyl group represents preferably lower alkanoyloxy-(ethyl, propyl or butyl), e.g. 2-acetyloxy- or 2-propionyloxy-(ethyl, propyl or butyl), 3-acetyloxy- or 3-propionyloxy-(propyl or butyl), 4-acetyloxy- or 4-propionyloxybutyl and the like.

A lower alkyloxy lower alkyl group represents preferably lower alkyloxy-(ethyl, propyl or butyl), e.g. 2-methoxy- or ethoxy-(ethyl, propyl or butyl), 3-methoxy- or 3-ethoxy-(propyl or butyl), 4-methoxy- or 4-ethoxybutyl and the like.

An aryloxy lower alkyl group represents preferably phenyloxy-(ethyl, propyl or butyl), said radicals being optionally substituted on the phenyl ring preferably by e.g. halogen, lower alkoxy or lower alkyl.

Lower alkyl quaternary derivatives of compounds of formula I are preferably, e.g. methyl, ethyl or propyl quaternary salts derived from reactive esters of lower alkanols having preferably from 1 to 4 carbon atoms, e.g. methanol, ethanol or propanol. The anions of said quaternary salts are preferably those corresponding to pharmaceutically acceptable acids such as halide, e.g. bromide or iodide; sulfate; or lower alkylsulfonate, e.g. methylsulfonate.

Although N-oxides or lower alkyl quaternary salts of compounds of formula I may represent such functionalized at one or more of any of the depicted ring nitrogen atoms in formula I, said N-oxides, lower alkyl quaternary salts of the compounds of formula I are preferably derived from those wherein $R_3$ is lower alkyl, aryl lower alkyl, or (hydroxy, lower alkanoyloxy, aryloxy or lower alkoxy)-lower alkyl having at least 2 carbon atoms in the lower alkyl group and wherein only the nitrogen atom bearing said $R_3$ substituent is thus functionalized.

Said compounds of Formula I form acid addition salts, which are preferably such of pharmaceutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycolic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, halogen substituted benzenesulfonic acid, p-toluenesulfonic, naphthalenesulfonic, sulfanilic or cyclohexylsulfamic acid.

Compounds of formula I with $R_1$ and/or $R_2$ being carboxy also form salts, preferably pharmaceutically acceptable salts, with bases which are preferably metal or ammonium salts, more particularly alkali or alkaline earth metal salts, e.g., the sodium, potassium, magnesium or calcium salt; or advantageously easily crystallizing ammonium salts derived from ammonia or organic amines, such as mono- di- or tri-lower(alkyl, cycloalkyl or hydroxy-alkyl)amines, lower alkylenediamines or lower hydroxyalkylamines, cyclic amines or (aralkyl)alkylammonium bases, e.g., methylamine, diethylamine, triethylamine, dicyclohexylamine, triethanolamine, ethylenediamine, tris-(hydroxymethyl)methylamine, piperidine, morpholine or benzyltrimethylammonium hydroxide.

The compounds of the invention exhibit valuable pharmacological properties, psychoactive, e.g. neuroleptic, as well as antiallergic, e.g. antihistaminic effects. Such are demonstrable in animal tests using advantageously mammals, e.g. mice, rats, guinea pigs or monkeys, as test objects. Said compounds can be applied to them enterally or parenterally, advantageously orally, or subcutaneously, intravenously or intraperitoneally, for example, within gelatin capsules or in the form of starchy suspensions or aqueous solutions respectively. The applied dosage may range between about 0.1 and 100 mg/kg/day, preferably between about 0.5 and 50 mg/kg/day, advantageously between about 1 and 30 mg/kg/day.

Said neuroleptic properties can be demonstrated in adult rats or squirrel monkeys, which were trained to press a lever to avoid the onset of an electric foot shock. Each lever press postpones the shock for 30 seconds. Whenever the animal fails to press the lever once within said period, brief (0.5 sec.) shocks are delivered at 15 second intervals until the animal again presses the lever. Under control conditions the animals press the lever at a moderately steady rate and seldom receive more then five or six shocks during a 25-minute (rats) and up to 4-hour experimental session. Said compounds are administered to the animals 30, 90, 210 minutes prior to the experimental session, and block the learned conditioned avoidance behavior, manifested by a decrease in avoidance responding with a marked increase in shocks taken by the animal. Both the avoidance responses and failures (shocks received) are recorded separately for evaluation.

Finally, said antihistaminic properties can be shown in vitro, e.g., according to Chasin et al., J. Neurochem. 22, 1031 (1974). Vesicles from a cell free preparation of guinea pig cerebral cortex are preincubated with $^3$H-adenine to form endogenous $^3$H-adenosine triphosphate. The vesicles are then incubated with 50 micromolar histamine to activate $^3$H-cyclic adenosine monophosphate synthesis in the absence or presence of the test compound at a concentration between 0.01 and 100 micromolar. When said compound is active, it inhibits the histamine activation of adenylate cyclase. The $IC_{50}$ represents the concentration at which histamine activation is inhibited by 50%.

Illustrative of the antipsychotic utility of the compounds of this invention, e.g, the compound of example 1, namely 5-(4-methyl-1-piperazinyl)-11H-imidazo[1,2-c][1,3]benzodiazepine disrupts avoidance behavior, e.g. decreases avoidance responses in rats and monkeys at an oral dose of 30 mg/kg or lower.

Illustrative of the antihistaminic activity, 5-(4-methyl-1-piperazinyl)-11H-imidazo[1,2-c][1,3]benzodiazepine, the compound of example 1, inhibits histamine activation of adenylate cyclase, with an $IC_{50}$ of about $1 \times 10^{-6}$M.

Furthermore, the compound of example 1, an illustrative example of this invention, is essentially free of extrapyramidal side effects, e.g. dyskinesias and dystonias in the monkey, and shows only minimal α-adrenergic blocking activity in vitro.

Accordingly, the compounds of the invention are useful neuroleptic and antihistaminic agents, for example, in the treatment or management of psychotic manifestations, e.g., aggression, agitation, schizophrenia, and/or allergic conditions in mammals, including man. They are also useful intermediates in the preparation of other valuable products, especially of pharmacologically active compositions.

The compounds of the invention are prepared e.g. according to the following method, which comprises: condensing a compound of formula III

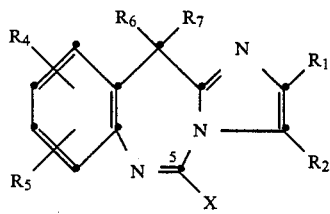

(III)

wherein X is a leaving group, preferably etherified mercapto, functionally modified hydroxy, cyanoto, thiocyanoto or nitroamino; and the remaining symbols have meaning as defined for formula I; with a compound of formula IV

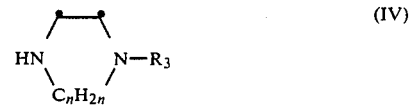

(IV)

or an alkali metal derivative thereof wherein $R_3$ has meaning as defined for formula I; and, if desired converting any resulting compound into another compound of the invention.

An etherified mercapto group is especially a mercapto group etherified by an optionally substituted hydrocarbon, particularly one of aliphatic character. It is expecially lower alkylthio, for example methylthio, ethylthio or butylthio, or phenyl-lower-alkylthio, for example benzylthio, or phenylthio. A functionally modified reactive hydroxy group is for example, an etherified or esterified hydroxy group, for example halogen, such as chloro or bromo, lower alkylsulfonyloxy, such as methanesulonyloxy, lower alkoxy such as methoxy or ethoxy, or di(lower-alkoxy)-phosphonyloxy such as diethoxyphosphonyloxy.

Preferred are the intermediates of formula III wherein X represents halogen, lower alkoxy, lower alkylthio, cyanoto or thiocyanoto.

Said condensation is advantageously carried out with an excess of the compound IV, or with equivalent amounts of said metal derivatives prepared in situ therefrom, preferably when X in formula III is halogeno, lower alkylthio or thiocyanato, advantageously and depending on the nature of said X, at temperatures between about 0° and 150°, and preferably in an appropriate solvent e.g. a lower alkanol such as amyl alcohol, dimethylformamide, hexamethylphosphoramide or toluene. Said condensation of a compound of formula III with a compound of formula IV may also be carried out in the presence of an acid, e.g., a hydrohalic acid such as hydrochloric acid.

The novel 11H-imidazo[1,2-c][1,3]benzodiazepine intermediates of formula III, e.g. wherein X is hydroxy or sulfhydryl are prepared according to ring closure procedures known per se, advantageously by condensing compounds of formula V

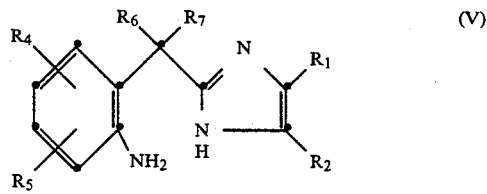

(V)

wherein $R_1$, $R_2$, $R_4$–$R_7$ have meaning as previously defined for formula I, with reactive carbonic acid derivatives such as phosgene, thiophosgene, 1,1'-carbonyldiimidazole, cyanogen bromide, phenyl chloroformate.

Compounds of formula III wherein X is hydroxy can be converted to compounds wherein X is sulfhydryl by conventional sulfurating agents, such as phosphorus pentasulfide.

Compounds of formula III, e.g. wherein X is hydroxy or sulfhydryl, can be further derivatized to compounds of formula III above wherein X has the meaning given above, according to methods known per se or, analogous to the procedures illustrated by the examples herein.

Starting materials of formula V are preferably prepared by reduction of the corresponding variously substituted 2-(o-nitrobenzyl)imidazoles, which are in turn preferably prepared from the correspondingly substituted o-nitrobenzylnitriles and 2-aminoacetals (or ketals), e.g. aminoacetaldehyde dimethyl acetal, by known methods illustrated in the examples herein.

The compounds of the invention are also advantageously prepared according to the following process comprising:

cyclizing a compound of formula VI

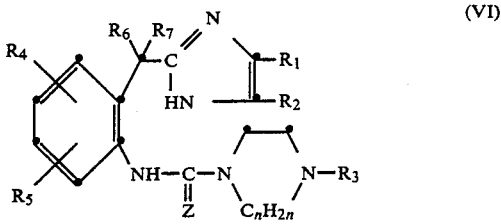

wherein Z is oxygen, sulfur, or NH, and the other symbols have the above-given meaning, under dehydrating, dehydrosulfurating or deamination conditions; and if desired converting any resulting compound into another compound of the invention.

Said cyclization is preferably carried out at temperatures between 0° and 120° and advantageously in an inert solvent, such as acetonitrile and toluene, with reagents such as phosphorous halides and/or oxyhalides e.g. phosphorous pentachloride or phosphorous oxychloride, or cyanogen halides e.g. cyanogen bromide, with or without crown ether catalysts, such as 8-crown-6-ether, and with or without basic catalysts such as triethylamine or potassium carbonate.

The starting materials of Formula VI can be obtained from precursors of Formula III or tautomers thereof, wherein X is hydroxy, thio or amino by condensing them with compounds of Formula IV in the presence or absence of other bases, e.g. those listed above, preferably in an inert solvent, such as methylene chloride or toluene at temperatures between 0° and 150°, advantageously between 10° and 50°. The ring opening reaction is preferably carried out at low temperature to minimize side reactions when $R_1$ and $R_2$ represent reactive functional groups.

Alternately, starting materials of formula VI, wherein $R_3$ is lower alkanoyl, lower alkoxycarbonyl or phenyl-lower-alkoxycarbonyl, are prepared by condensing a compound of formula V above with a compound of formula VII

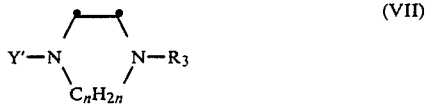

wherein Y' represents halocarbonyl, halothiocarbonyl or cyano, and $R_3$ represents lower alkanoyl, lower alkoxycarbonyl or lower phenylalkoxycarbonyl, preferably in an inert solvent, at temperatures between about 0° and 150°, with or without basic catalysts such as triethylamine or potassium carbonate.

Starting materials of formula VII are preferably obtained by reacting compounds of formula IV wherein $R_3$ represents lower alkanoyl, lower alkoxycarbonyl or lower phenylalkoxycarbonyl, or advantageously e.g. the N-trimethylsilyl derivative thereof, with e.g. phosgene, thiophosgene or cyanogen bromide in an inert solvent such as ethyl ether, methylene chloride or dimethoxyethane at temperatures of about −70° to +50° with or without basic catalysts such as triethylamine or potassium carbonate.

The compounds of the invention so obtained can be converted into other compounds of Formula I according to known methods. Thus, for example, those with $R_3$ being hydrogen or alkali metal, e.g., sodium or lithium salts thereof, can be reacted with substituted or unsubstituted oxiranes, such as ethylene oxide, or reactive esters of unsubstituted or correspondingly substituted aliphatic or araliphatic alcohols such as methanol, ethanol, methoxyethanol, phenoxyethanol, allyl alcohol, propargyl alcohol, e.g. such esterified by a strong inorganic or organic acid, above all hydrohalic acids, e.g. hydrochloric, hydrobromic or hydriodic acid; sulfuric or an aromatic sulfonic acid, e.g. p-toluene or m-bromobenzene sulfonic acid, in order to obtain the corresponding N-substituted compounds or quaternaries respectively, depending on the molar amount of the alkylating agent employed. Intermediates of formula I wherein $R_3$ is alkali metal or alkali metal derivatives of compounds of formula IV are obtained by metallation with reactive organometallic agents such as lithium diisopropylamide, with alkali metal alkoxides such as sodium methoxide, or alkali metal hydrides such as sodium or potassium hydride.

Unsaturated compounds, such as those with $R_3$ being lower alkenyl, lower alkynyl may be hydrogenated with catalytically activated hydrogen to obtain compounds wherein $R_3$ is the corresponding lower alkyl. Conversely, resulting N-alkylated compounds can be converted into N-unsubstituted compounds, e.g. by catalytic hydrogenolysis of N-benzyl compounds, or reaction of N-lower alkyl derivatives with lower alkyl haloformates, e.g. ethyl chloroformate, to yield N-acyl derivatives which, in turn, may be hydrolyzed to said unsubstituted compounds, those with $R_3$=H, for example with aqueous bases, such as alkali metal hydroxides, e.g. aqueous sodium hydroxide solution.

Compounds of formula I wherein $R_3$ is hydroxylower alkyl can also be prepared by first reacting corresponding compounds of Formula I, wherein $R_3$ represents hydrogen, with reactive derivatives of corresponding glycols, glycolic acids or dicarboxylic acids, such as lower alkyl esters, halides or anhydrides thereof, or reactive esters of said glycols or glycolic acids derivatives, for example with hydrohalic or aromatic sulfonic acids, 1,2-dibromoethane or -propane, ethyl bromoacetate or -propionate, ethyl tosyloxyacetate, diethyl oxalate or malonate or ethyl oxalyl chloride. The intermediates so obtained are either hydrolyzed or reduced with simple or complex light metal hydrides such as lithium aluminum hydride, alone or with diborane to compounds of formula I wherein $R_3$ is hydroxyalkyl.

Compounds of formula I wherein $R_3$ is lower alkyl, e.g. methyl can be prepared by reacting the corresponding compounds of formula I wherein $R_3$ represents hydrogen with lower alkyl or phenyl lower alkyl haloformates, such as ethyl chloroformate, to obtain compounds of formula I wherein $R_3$ is lower alkoxycarbonyl or lower phenylalkyloxycarbonyl, and reducing said acyl derivatives with simple or complex light metal hydrides such as lithium aluminum hydride, sodium bis-(2-methoxy-ethoxy)aluminum hydride, or sodium tri-t-butoxyaluminum hydride.

N-acylated derivatives of formula I wherein $R_3$ is lower alkanoyl can preferably be obtained from compounds of formula I with $R_3$ being hydrogen and corresponding reactive carboxylic acid derivatives, e.g., halides, simple or activated esters, such as alkyl or cyanoalkyl esters or anhydrides. These in turn can be reduced as above to the compounds of formula I wherein $R_3$ is lower alkyl. Compounds of formula I wherein $R_3$ is hydroxy lower alkyl may be acylated as above to the compounds wherein $R_3$ is lower alkanoyloxy lower alkyl.

Compounds of Formula I with $R_1$ and/or $R_2$ being hydrogen, may be converted to the corresponding compounds with $R_1$ and/or $R_2$ being halogen or acyl, e.g. by halogenation, preferably with chlorine in acetic acid or by acylation under Friedel-Crafts conditions with e.g. a lower alkanoyl halide, a lower alkyl haloformate, a trihaloacetyl halide or a halosulfonic acid optionally followed by treatment with an alkali metal lower alkoxide, hydroxide or amide. Any resulting carboxylic or sulfonic acid derivatives may then be hydrolyzed in known fashion, preferably under alkaline conditions and/or amidized with ammonia, mono- or di-lower alkylamines; the resulting primary carboxamides may in turn be dehydrated to the corresponding nitriles according to conventional methods.

Compounds of the formula I in which $R_1$ and/or $R_2$ represents carboxy, can be prepared, for example, by hydrolysis of compounds wherein $R_1$ and/or $R_2$ represents cyano, lower alkoxycarbonyl or carbamoyl.

Tertiary amines in which $R_3$ differs from hydrogen and is e.g. lower alkyl, aryl lower alkyl, can be converted into the N-oxides, for example with hydrogen peroxide or organic peracids, such as lower peralkanoic or perbenzoic acids, e.g. peracetic or m-chloroperbenzoic acid, advantageously at temperatures at or below room temperature with the latter, or up to 100° with hydrogen peroxide in the presence of lower alkanoic acids, e.g. acetic acid. If only a mono N-oxide is desired, care should be taken in order to prevent further oxidation.

Finally, the compounds of the invention are either obtained in the free form, or as a salt thereof. Any resulting base can be converted into a corresponding acid addition salt, preferably with the use of acids which yield a pharmaceutically acceptable salt, or with an anion exchange preparation, or any resulting salt can be converted into the corresponding free base, for example, with the use of a stronger base, such as a metal or ammonium hydroxide or a basic salt, e.g. an alkali metal hydroxide or carbonate, or a cation exchange preparation. Said acid addition salts are preferably such of pharmaceutically acceptable inorganic or organic acids described previously.

Compounds of formula 1 with $R_1$ and/or $R_2$ being carboxy can be converted into the corresponding metal or ammonium salts by e.g. treatment with the alkaline or alkaline earth metal hydroxides or carbonates, ammonia or the amines listed previously.

These or other salts, for example, the picrates, can also be used for purification of the bases obtained; the bases are converted into salts, the salts are separated and the bases are liberated from the salts.

In view of the close relationship between the free compounds and the compounds in the form of their salts, whenever a compond is referred to in this context, a corresponding salt is also intended, provided such is possible or appropriate under the circumstances.

In case mixtures of geometrical or optical isomers of the above compounds, e.g. I to VII are obtained, these can be separated into the single isomers by methods in themselves known, e.g. by fractional distillation, crystallization and/or chromatography. Racemic products can likewise be resolved into the antipodes, for example, by separation of diastereomeric salts thereof, e.g. by the fractional crystallization of the salts formed with d- or l-tartaric acid, mandelic acid, cinchonidine and the like.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds, indicated above as being especially valuable, e.g. those of Formula II.

The pharmacologically active compounds of the invention are useful in the manufacture of pharmaceutical compositions comprising an effective amount thereof in conjunction or admixture with excipients suitable for ether enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 Kg weight may contain between about 25 and 200 mg of the active ingredient.

The following examples are intended to illustrate the invention and are not to be construed as being limitations thereon. Temperatures are given in degrees Centigrade, and all parts whenever given are parts by weight. If not mentioned otherwise, all evaporations are performed under reduced pressure, preferably between

EXAMPLE 1

5-(4-methyl-1-piperazinyl)-11H-imidazo[1,2-c][1,3]benzodiazepine

Amyl alcohol (5100 ml) and 918.35 g (9.17 moles) of N-methylpiperazine are charged into a 12 liter 3-necked reaction flask fitted with a Dean-Stark adapter. The solution is stirred under nitrogen atmosphere and 989 ml of 10N ethanolic hydrogen chloride solution are added rapidly. The reaction mixture is heated to reflux and the distillate is collected in the Dean-Stark adapter. When the temperature of the reaction mixture reaches 131° the Dean-Stark adapter is removed and an additional 918.35 g (9.17 moles) of N-methylpiperazine followed by 1045.0 g (4.56 moles) of 5-methylthio-11H-imidazo[1,2-c][1,3]benzodiazepine are added. The mixture is heated at reflux under nitrogen atmosphere for 20 hours. Amyl alcohol is then removed under reduced pressure at a water bath temperature of 80°. The viscous residual oil is dissolved in 10,000 ml of dichloromethane, washed with 3×4,000 ml of 4N sodium hydroxide and 6×4,000 ml of water. The dichloromethane solution is then extracted with 3×2,000 ml of 6N hydrochloric acid. The aqueous solution is back washed with 2×2,000 ml of dichloromethane, treated with 100 g of activated carbon and filtered. The clear filtrate is adjusted to pH 9-10 with 1,500 ml of ammonium hydroxide solution (29%). The oil which separates is extracted with 3×4,000 ml of dichloromethane, the extracts are dried over 1,000 g of sodium sulfate and the solvent removed at reduced pressure with a water bath temperatures of 60°. An oil is obtained which rapidly solidifies and after drying further (5 mm Hg/40°) yields crude product, m.p. 113°-120°. The crude product is dissolved in 8,000 ml of hot (60°-70°) isopropanol. The solution is decolorized with 200 g of activated carbon and filtered. To this solution is added a solution of 760.7 g (8.28 moles) of maleic acid in 2,500 ml of warm (30°) isopropanol and the meleate salt begins to precipitate. The suspension is stirred overnight at ambient temperature to complete crystallization and the solid is collected by filtration. The product is washed with 3×500 ml of cold isopropanol and dried (0.5 mm/50°). This is recrystallized from ethanol, the resulting product is washed first with ethanol and then with ether and then dried to give 5-(4-methyl-1-piperazinyl)-11H-imidazo[1,2-c][1,3]benzodiazepine monomaleate, m.p. 204°-205° (dec).

A solution of 2,246 g of the above maleate salt in 9000 ml of water is treated with 100 g of activated carbon and filtered. The aqueous solution is adjusted to pH9 with 1000 ml of 29% ammonium hydroxide and the free base separates as an oil. The oil is extracted with 3×2000 ml of dichloromethane, the extract is dried over sodium sulfate, filtered and the solvent is removed under reduced pressure at a water bath temperature of 40°. The solid obtained is recrystallized from 14,130 ml of heptane. The light yellow solid is collected and washed with 2×500 ml of heptane and dried (0.01 mm/50°) to give 5-(4-methyl-1-piperazinyl)-11H-imidazo[1,2-c][1,3]benzodiazepine, m.p. 124°-4°, the compound of formula II wherein $R_1$, $R_2$ and $R_4$ are hydrogen, $C_nH_{2n}$ is $CH_2CH_2$ and $R_3$ is methyl.

The starting material is prepared as follows:

Absolute ethanol (24,000 ml) and 3,240 g (60.0 moles) of sodium methoxide are charged into a 20 gallon reaction flask. The solution is stirred under nitrogen while a solution of 8228.4 g (60.0 moles) of o-nitrotoluene and 8768.4 g (60.0 moles) of diethyl oxalate is added all at once. The resulting solution is heated at reflux for 25 minutes, cooled to 60° with an ice-bath and 18,000 ml of water are cautiously added. Heat is then applied and the mixture is held at the reflux temperature for 1 hour. Most of the ethanol is then removed. The turbid solution is cooled at 50° and a solution of 4,140 g (59.6 moles) of hydroxylamine hydrochloride in 6,000 ml of water is added all at once. The temperature is maintained at 50°, the pH is adjusted to 7.0 with 6,000 ml of 10N sodium hydroxide solution and the reaction mixture stirred overnight at ambient temperature. The suspension is cooled to 10° and the pH is adjusted to 1.0 with 6,000 ml of 12N hydrochloric acid. The stirring is continued overnight at 10° to complete the liberation of the free acid. The solid is collected, washed with 6×4,000 ml of water, air dried overnight and suspended in 20,000 ml of toluene. The suspension is stirred for 1 hour under nitrogen atmosphere. The product is collected, washed with 4×2,000 ml of toluene followed by 4×2,000 ml of petroleum ether and dried (5 mm Hg/60°) to give 2-nitrophenylpyruvic acid oxime, m.p. 158°-60° (dec).

Water (50,000 ml), 2,940 ml of glacial acetic acid and (22.22 moles) of 2-nitrophenylpyruvic acid oxime are charged into a 20 gallon reactor. The stirred suspension is heated over two hours under nitrogen atmosphere to 90° and this temperature is maintained for 2 hours. The dark solution is allowed to cool slowly and is stirred overnight at ambient temperature. The suspension is extracted with 5×4,000 ml of methylene chloride, washed with 3×3,000 ml of water, dried over magnesium sulfate and filtered. The filtrate is treated with activated carbon, filtered and the solvent is removed under reduced pressure. The solid residue is recrystallized from 1,000 ml of isopropanol to give 2-nitrophenylacetonitrile, m.p. 82°-84°.

Absolute ethanol (2,250 ml) and 1,500 g (9.25 moles) of o-nitrophenylacetonitrile are charged into a 22 liter flask. The suspension is cooled to 5°-10° and hydrogen chloride is bubbled into the mixture for 2.5 hours. The reaction mixture is stirred at 10° under nitrogen atmosphere overnight. It was then diluted with 16,000 ml of ether and stirred for 1 hour; the solid is collected by filtration, washed with 4×1,000 ml of ether and dried (5 mm Hg/40°) to give ethyl 2-(2-nitrophenyl)acetimidate hydrochloride, m.p. 122°-123° (dec).

Ethanol (2,200 ml) and 5,156 g (8.81 moles) of ethyl 2-(2-nitrophenyl)acetimidate hydrochloride are charged into a 22 liter flask. The suspension is stirred under nitrogen at room temperature and 1022.9 g (9.73 moles) of aminoacetaldehyde dimethylacetal are added all at once. The mixture is stirred for 1 hour and 1,693 ml of 12N hydrochloric acid are added all at once to cause a gentle exotherm (to 40°). Heat is then applied and the temperature is maintained at 70°-80° for 30 minutes. The solution is cooled to 20° (ice-water bath) and diluted with 2,700 ml of 10N sodium hydroxide solution to precipitate the product. The suspension is stirred at 10° for 1 hour under nitrogen atmosphere, the solid collected by filtration and washed with 3×2,000 ml of water to give 2-(2-nitrobenzyl)imidazole, m.p. 155°-7°.

50% Aqueous ethanol (5,672 ml) and 2,890 g (14.22 moles) of 2-(2-nitrobenzyl)imidazole are charged into a 22 liter flask. The suspension is stirred under nitrogen atmosphere and 2,400 g (42.97 moles) of iron powder (100 mesh) are added all at once. The mixture is then warmed to 70° and a solution of 1.7 ml of 12N hydrochloric acid in 8.3 ml absolute ethanol are added. A vigorous exotherm results and a strong reflux occurs that persists for 1.5 hours. When the exotherm subsides, a mixture of 290 ml of 12N HCl and 1400 ml of absolute ethanol are added over 30 minutes. Heat is applied and the mixture is refluxed for 2 hours, diluted with 6,500 ml of absolute ethanol and adjusted to pH 8–9 with 700 ml of 10N sodium hydroxide. The suspension is stirred for 1 hour and filtered. The cake is washed with 1,000 ml of absolute ethanol, the filtrates are combined and the solvent is removed. The remaining solid is then suspended in 10,000 ml of water, stirred under nitrogen atmosphere for two hours, collected, washed with 2,000 ml of water, and dried to yield 2-(2-aminobenzyl)imidazole, m.p. 153°–155°.

Dichloromethane (42,000 ml) and 5,120 g (50.65 moles) of triethylamine are charged into a 20 gallon flask. The solution is stirred under nitrogen atmosphere and 4,370 g (25.23 moles) of 2-(2-aminobenzyl)imidazole were added. The suspension is cooled to 0°–5° and 3,421 g (29.75 moles) of 85% thiophosgene in carbon tetrachloride are added over 3 hours, during which time the reaction temperature rises slowly to 15°. The suspension is then stirred at 10° for 4 hours and at ambient temperature overnight. The precipitated product is collected, washed with 2×3000 ml of dichloromethane and 5×4000 ml of water, and dried (5 mm Hg/60°) to give 11H-imidazo[1,2-c][1,3]benzodiazepine-5(6H)-thione, m.p. 182°–183°.

Absolute ethanol (20,000 ml) is charged into a 20 gallon flask and stirred under nitrogen atmosphere; 517.62 g (9.58 moles) of sodium methoxide are added. After stirring for 30 minutes there is complete solution and 2,063 g (9.58 moles) of 11H-imidazo[1,2-c][1,3]benzodiazepine-5(6H)-thione are added. There is complete solution after stirring at room temperature for 1 hour. The solution is then cooled to 1°, and 1,360 g (9.58 moles) of methyl iodide are added over 30 minutes. The reaction mixture is stirred at 5° for 4 hours and at ambient temperature overnight. The turbid solution is then cooled to 5° and diluted with 50,000 ml of water. The resulting suspension is stirred for 4 hours at 5°. The solid is collected, and dried (5 mm Hg/60°) to give 5-methylthio-11H-imidazo[1,2-c][1,3]benzodiazepine, m.p. 87°–8°.

Similarly prepared from 4-chloro-2-nitrophenylacetonitrile is 8-chloro-11H-imidazo[1,2-c][1,3]benzodiazepine-5(6H)-thione, m.p. 200°–201° and 8-chloro-5-methylthio-11H-imidazo[1,2-c][1,3]benzodiazepine hydrochloride, m.p. 255°–7°.

The following starting materials are similarly prepared from the correspondingly substituted 2-nitrophenylacetonitriles:
8-methyl-5-methylthio-11H-imidazo[1,2-c][1,3]benzodiazepine;
8-fluoro-5-methylthio-11H-imidazo[1,2-c][1,3]benzodiazepine;
8-methoxy-5-methylthio-11H-imidazo[1,2-c][1,3]benzodiazepine.

EXAMPLE 2

To a suspension of 2.46 g of 1-[2-(2-imidazolylmethyl)phenylcarbamoyl]-4-methylhomopiperazine in 19.4 ml of phosphorus oxychloride is added at once 1.66 g of phosphorous pentachloride and the mixture is stirred at room temperature for 4 hours. The mixture is evaporated to dryness, the residue is suspended in 45.2 ml of methylene chloride, the suspension is cooled to 0° and 21.4 ml of triethylamine are added dropwise with stirring over a period of 15 minutes. The mixture is allowed to warm up to room temperature, stirred for 1.5 hours and poured into 10% aqueous potassium carbonate. The methylene chloride layer is separated, the aqueous layer is washed with methylene chloride and the combined methylene chloride extracts are dried over MgSO$_4$, decolorized with charcoal and evaporated to dryness. The residue is purified by column chromatography with 50 g of silica gel, using methylene chloride-methanol-conc. ammonium hydroxide (300:50:1) as eluent to give 5-(4-methyl-1-homopiperazinyl)-11H-imidazo[1,2-c][1,3]benzodiazepine as an oil. This free base is dissolved in acetone and treated with maleic acid to give 5-(4-methyl-1-homopiperazinyl)-11H-imidazo[1,2-c][1,3]benzodiazepine monomaleate, m.p. 160°–163°.

5-(4-Methyl-1-piperazinyl)-11H-imidazo[1,2-c][1,3]benzodiazepine monomaleate of example 1 is similarly prepared from 1-[2-(2-imidazolylmethyl)phenylcarbamoyl]-4-methylpiperazine.

The starting materials are prepared as follows:

A solution of 32.4 g of phenyl chloroformate in 100 ml of acetonitrile is added dropwise under nitrogen while stirring to a mixture of 34.6 g of 2-(2-aminobenzyl)imidazole and 71 g of triethylamine in 600 ml of acetonitrile at room temperature. After addition is complete, the reaction mixture is heated under reflux for 12 hours, and allowed to cool to room temperature. Water (150 ml) is added, the mixture is stirred at room temperature for 0.5 hour and cooled to 5°. The resulting precipitate is filtered off, washed first twice with 50 ml of water, then 3 times with 33 ml of cold acetone and dried to give 11H-imidazo[1,2-c][1,3]benzodiazepin-5-(6H)-one, m.p. 255°–7°.

Alternately, 0.75 g of 1,1'-carbonyldiimidazole is added at once to a suspension of 0.79 g of 2-(2-aminobenzyl)imidazole in 38 ml of methylene chloride and the mixture is stirred at room temperature overnight. The resulting precipitate is collected and recrystallized from methylene chloride to give the crude 11H-imidazo[1,2-c][1,3]benzodiazepin-5(6H)-one, m.p. 238°–40°.

In analogous fashion, or by using phosgene as the reagent for cyclization, the following intermediates are obtained:

(a) 2,3-dimethyl-11H-imidazo[1,2-c][1,3]benzodiazepin-5-(6H)-one;
(b) 8-chloro-11H-imidazo[1,2-c][1,3]benzodiazepin-5(6H)-one;
(c) 8-methyl-11H-imidazo[1,2-c][1,3]benzodiazepin-5(6H)-one;
(d) 8-methoxy-11H-imidazo[1,2-c][1,3]benzodiazepine-5(6H)-one.

To a suspension of 0.76 g of 11H-imidazo[1,2-c][1,3]benzodiazepin-5-(6H)-one in 9 ml of methylene chloride is added at once 0.41 g of N-methylhomopiperazine and the mixture is stirred at room temperature for 24 hours. The reaction mixture is filtered and the filtrate is evaporated to dryness. Recrystallization of the residue from methylene chloride-ether gave 1-[2-(2-imidazolylmethyl)phenylcarbamoyl]-4-methylhomopiperazine, the compound of formula VI wherein $R_1$, $R_2$, $R_4$–$R_7$ are hydrogen, $C_nH_{2n}$ is $(CH_2)_3$, $R_3$ is methyl and Z is oxygen, melting at 139°–143°.

Similarly prepared from N-methylpiperazine is 1-[2-(2-imidazolylmethyl)phenylcarbamoyl]-4-methylpiperazine, m.p. 172°–4°.

The following compounds are prepared according to the above procedures:
1-[2-(4,5-dimethyl-2-imidazolylmethyl)phenylcarbamoyl]-4-methylpiperazine; and
1-[2-(2-imidazolylmethyl)-5-chlorophenylcarbamoyl]-4-methylpiperazine.

EXAMPLE 3

A solution of 2.4 g of 5-cyanomercapto-11H-imidazo[1,2-c][1,3]benzodiazepine in 5 ml of hexamethylphosphoramide is cooled to −5° and 2.1 g of N-methylpiperazine is added dropwise with efficient mechanical stirring and under nitrogen, over a period of 5 minutes. Stirring is continued for 10 minutes at −5° and another 10 minutes after removal of the cooling bath. The mixture is diluted with 100 ml of ethyl acetate and the solution washed twice with brine, dried (MgSO$_4$), and evaporated to dryness. To the residue, a solution of 1.2 g of maleic acid in 3 ml acetone is added and the mixture is diluted with ether. The crude product crystallizes, m.p. 183°–186°, and is recrystallized to give the 5-(4-methyl-1-piperazinyl)-11H-imidazo[1,2-c][1,3]benzodiazepine monomaleate of example 1.

The starting material is prepared as follows:

Sodium hydride (50% in mineral oil, 1.44 g,) is washed with dry ether and suspended in 100 ml of dry tetrahydrofuran; 6.45 g of 11H-imidazo[1,2-c][1,3]benzodiazepine-5(6H)-thione is added in portions to the suspension of sodium hydride, with stirring and under nitrogen, over a period of 2 minutes. The mixture is stirred at room temperature for 1.5 hours. The white suspension, which is formed by the end of this time, is cooled to 0° and 3.5 g of cyanogen bromide dissolved in 10 ml of dry tetrahydrofuran is added dropwise. The mixture is stirred at room temperature for 0.5 hour and evaporated under reduced pressure at 45°. The residue is dissolved in methylene chloride, the solution is washed with water, dried (MgSO$_4$), decolorized with charcoal, and evaporated to a small volume. 5-Cyanomercapto-11H-imidazo[1,2-c][1,3]benzodiazepine, m.p. 111°–113°, crystallizes on dilution with ether.

EXAMPLE 4

To a solution of 8.9 g of 1-[2-(2-imidazolylmethyl)phenylthiocarbamoyl]-4-ethoxycarbonylpiperazine in 70 ml of acetonitrile, cooled to 0°, is added 2.4 g of solid potassium carbonate while stirring, followed by dropwise addition of a solution of 2.5 g of cyanogen bromide in 10 ml of acetonitrile; the mixture is allowed to warm up to room temperature overnight. The solids are filtered off, washed with ethyl acetate, and the filtrate is evaporated to dryness. The residue is dissolved in methylene chloride, the solution is washed with water, dried over M$_g$SO$_4$, decolorized with charcoal and evaporated to dryness. The residue is chromatographed with 250 g of silica gel using ethyl acetate-methanol (9:1) as eluant to give 5-(4-ethoxycarbonyl-1-piperazinyl)-11H-imidazo[1,2-c][1,3]benzodiazepine, m.p. 137°–139°.

The starting material is prepared as follows:

A solution of 20 g of 1-ethoxycarbonylpiperazine in 400 ml dry tetrahydrofuran is cooled to −65° and 61.5 ml of 2.1M solution of n-butyllithium in hexane is added dropwise over a period of 15 minutes. The mixture is stirred for 15 minutes and a solution of 16.44 ml of chlorotrimethylsilane in 68 ml of tetrahydrofuran is added dropwise over a period of 15 minutes. The mixture is then allowed to warm up to room temperature overnight and evaporated to dryness. Ethyl ether is added, the solids are filtered off, the filtrate is evaporated to dryness and the residue is distilled to give 1-ethoxycarbonyl-4-trimethylsilylpiperazine, b.p. 102°–107°/0.1 mm/Hg.

To a solution of 4.66 ml of 85% thiophosgene in 200 ml of ethyl ether, cooled to −76° is added, while stirring and under nitrogen, a solution of 7 g of 1-ethoxycarbonyl-4-trimethylsilylpiperazine in 35 ml of ethyl ether over a period of 20 minutes. The mixture is allowed to warm up to room temperature overnight. The suspension is filtered and the filtrate is evaporated to dryness. The residue is crystallized from methylene chloridehexane to give 4-ethoxycarbonyl-1-piperazinyl-thiocarbonyl chloride, m.p. 107°–111°.

To a suspension of 3.8 g of 2-(2-aminobenzyl)imidazole in 38 ml of tetrahydrofuran and 3.23 ml of triethylamine is added dropwise a solution of 5.5 g of 4-ethoxycarbonyl-1-piperazinyl-thiocarbonyl chloride in 10 ml of methylene chloride at room temperature. The mixture is stirred for 1 week and the suspension filtered. The filtrate is washed with first 10% aqueous potassium carbonate, then with water, dried and evaporated to dryness to give amorphous 1-[2-(2-imidazolylmethyl)phenylthiocarbamoyl]-4-ethoxycarbonylpiperazine, characterized by NMR.

EXAMPLE 5

According to the methods illustrated by the previous examples, the following compounds of formula II wherein R$_1$ and R$_2$ represent hydrogen, and C$_2$H$_{2n}$ represents CH$_2$CH$_2$ are obtained from equivalent amounts of the corresponding starting materials.

| No. | R$_3$ | R$_4$ | Salt | m.p. |
|-----|-------|-------|------|------|
| 1 | CH$_2$CH$_2$OH | H | — | 143–4° |
| 2 | CH$_2$CH$_2$OH | Cl | HCl | 225° dec. |
| 3 | CH$_3$ | Cl | 2HCl | 226–8° dec. |
| 4 | CH$_3$ | H | 2HCl | >250° dec. |
| 5 | CH$_3$ | H | HCl | 217–20° |

EXAMPLE 6

The mixture of 315 mg of 1-[2-(2-imidazolylmethyl)phenylthiocarbamoyl]-4-methylpiperazine, 3.3 ml of dimethylformamide, 276 mg of potassium carbonate, 116 mg of cyanogen bromide and 50 mg of 8-crown-6 ether is stirred at room temperature under nitrogen for 3 hours. It is diluted with ethyl acetate, washed with saturated aqueous sodium chloride, dried and evaporated. The residue is dissolved in acetone, the solution treated with 116 mg of maleic acid and diluted with diethyl ether, to yield 5-(4-methyl-1-piperazinyl)-11H-imidazo[1,2-c][1,3]benzodiazepine monomaleate of example 1.

The starting material is prepared as follows:

The mixture of 2.1 g of 11H-imidazo[1,2-c][1,3]benzodiazepine-5(6H)-thione, 23 ml of methylene chloride and 1.0 g of 1-methylpiperazine is stirred at room temperature for 15 hours. The crystalline product formed is filtered off and washed with methylene chloride, to yield 1-[2-(2-imidazolylmethyl)phenylthiocarbamoyl]-4-methylpiperazine.

EXAMPLE 7

To a solution of 0.2 g of 5-(4-carboethoxy-1-piperazinyl)-11H-imidazo[1,2-c][1,3]benzodiazepine in 2 ml of dry tetrahydrofuran, 100 mg of lithium aluminum hydride are added at once and the mixture is refluxed under nitrogen for 48 hours. The mixture is cooled to room temperature, stirred with 0.2 ml of 30% sodium hydroxide, and filtered. the filtrates are evaporated to dryness and the product is purified to give 5-(4-methyl-1-piperazinyl)-11H-imidazo[1,2-c][1,3]benzodiazepine.

EXAMPLE 8

To a solution of 100 mg of 5-(4-benzyloxycarbonyl-1-piperazinyl)-11H-imidazo[1,2-c][1,3]benzodiazepine in 0.3 ml of acetic acid are added 0.35 ml of a 2N solution of hydrobromic acid in acetic acid. The mixture is heated at 100° for 1 hour and stirred at room temperature overnight. Ether is added, and the 5-(4H-1-piperazinyl)-11H-imidazo[1,2-c][1,3]benzodiazepine hydrobromide precipitates.

The starting material is prepared similarly to starting material of example 4 by replacing 1-ethoxycarbonyl-piperazine with the equivalent amount of 1-benzyloxycarbonylpiperazine.

EXAMPLE 9

A mixture of 265 mg of 5-(4H-1-piperazinyl)-11H-imidazo[1,2-c][1,3]benzodiazepine 0.5 g of potassium carbonate, 0.142 g of methyl iodide and 2 ml of acetone is stirred at room temperature overnight and evaporated. Water is added to the residue, and the mixture is extracted with methylene chloride. The extracts are dried over magnesium sulfate, evaporated, and the residue is purified to give 5-(4-methyl-1-piperazinyl)-11H-imidazo[1,2-c][1,3]benzodiazepine.

EXAMPLE 10

The following compounds of formula I ($R_5$–$R_7$=H) are prepared according to the methods illustrated by the previous examples and are obtained from equivalent amounts of the corresponding substituted starting materials.

| No. | $R_1$ | $R_2$ | $R_3$ | $R_4$ | $C_nH_{2n}$ |
| --- | --- | --- | --- | --- | --- |
| 1 | $CH_3$ | H | $CH_3$ | H | $(CH_2)_2$ |
| 2 | $CH_3$ | $CH_3$ | $CH_3$ | H | $(CH_2)_2$ |
| 3 | H | H | $CH_3$ | 8-$CF_3$ | $(CH_2)_2$ |
| 4 | H | H | $CH_3$ | 8-F | $(CH_2)_2$ |
| 5 | H | H | $CH_3$ | 8-$OCH_3$ | $(CH_2)_2$ |
| 6 | H | H | $CH_3$ | 8-OH | $(CH_2)_2$ |
| 7 | H | H | $CH_3OCH_2CH_2$ | H | $(CH_2)_2$ |
| 8 | H | H | $CH_3COOCH_2CH_2$ | H | $(CH_2)_2$ |
| 9 | H | H | $CH_3$ | 8-$CH_3$ | $(CH_2)_2$ |

EXAMPLE 11

Preparation of 10,000 tablets each containing 25 mg of the active ingredient:

Formula

| | |
| --- | --- |
| 5-(4-methyl-1-piperazinyl)-11H—imidazo[1,2-c]-[1,3]benzodiazepine | 250.00 g |
| Lactose | 957.00 g |
| Corn Starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 12

Preparation of 10,000 capsules each containing 50 mg of the active ingredient:

Formula

| | |
| --- | --- |
| 5-(4-methyl-1-piperazinyl)-11H—imidazo[1,2-c][1,3]-benzodiazepine monomaleate | 500.0 g |
| Lactose | 1,400.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

Analogously tablets or capsules are prepared from the remaining compounds of the invention, e.g. those illustrated by the other examples herein.

EXAMPLE 13

A mixture of 10 g of 1-[2-(4-methyl-2-imidazolylmethyl)phenylcarbamoyl]-4-methylpiperazine, 86 ml of phosphorous oxychloride and 7.24 g of phosphorous pentachloride is stirred at room temperature for 4 hours and evaporated to dryness. The residue is suspended in 186 ml of methylene chloride and 55.2 ml of triethylamine is added dropwise at 0° over a period of 15 minutes. The mixture is stirred at room temperature overnight, poured into cold water, basified with 10% aqueous potassium carbonate and extracted with methylene chloride. The methylene chloride extracts are re-extracted with 2N hydrochloric acid. The acidic extracts are basified with 2N aqueous sodium hydroxide and extracted three times with methylene chloride. The organic extracts are dried over magnesium sulfate, decolorized with charcoal and evaporated to dryness. The residue is chromatographed from 180 g of silica gel using methylene chloride-methanol-ammonium hydroxide (300:50:1) as eluant to give a foamy material which is dissolved in acetone and treated with an equivalent amount of maleic acid to give on dilution with ether the 2-methyl-5-(4-methyl-1-piperazinyl)-11H-imidazo[1,2-c][1,3]benzodiazepine mono-maleate, m.p. 195°–197°.

The starting material is prepared as follows:

A solution of ethanolic sodium ethoxide, prepared by dissolving 4.48 g of sodium metal in 112 ml of absolute ethanol, is added dropwise to a suspension of 47.84 g of ethyl 2-(2-nitrophenyl)acetimidate hydrochloride in 224 ml of ethanol and the mixture is stirred at room temperature for one hour. The sodium chloride formed is filtered, 22.82 g of the ethylene ketal of 1-amino-2-propanone is added to the filtrates and the mixture is stirred at room temperature overnight. The insoluble material is filtered off and the filtrates are evaporated to dryness. The residue is dissolved in 470 ml of concentrated hydrochloric acid and the solution is refluxed for 1 hour. The mixture is washed once with ether, basified with 2N sodium hydroxide and extracted three times with ethyl acetate. The extracts are dried over magnesium sulfate, decolorized with charcoal and evaporated. The residue is crystallized from methylene chloride-ether to give 4-methyl-2-(2-nitrobenzyl)imidazole, m.p. 125°–128°.

A mixture of 23.44 g of 4-methyl-2-(2-nitrobenzyl)imidazole, 2.34 g of 10% palladium on charcoal and 234 ml of ethanol is hydrogenated at 42 psi (3 atmospheres) at room temperature for 4 hours. The catalyst is filtered and the filtrates are evaporated to dryness to give 4-methyl-2-(2-aminobenzyl)imidazole showing signals in the NMR spectrum at δ 2.09, 3.78, 6.08.

A mixture of 18.61 g of 4-methyl-2-(2-aminobenzyl)imidazole, 16.12 g of 1,1'-carbonyldiimidazole and 375 ml of methylene chloride is stirred at room temperature overnight. The methylene chloride is evaporated to a small volume, the mixture is cooled to 0° and the solids are filtered and washed with ether to give 2-methyl-11H-imidazo[1,2-c][1,3]benzodiazepine-5(6H)-one, m.p. 234.5°–236.5°.

A mixture of 16 g of 2-methyl-11H-imidazo[1,2-c][1,3]benzodiazepine-5-(6H)-one, 9.58 g of N-methylpiperazine and 160 ml of methylene chloride is stirred at room temperature overnight. The mixture is decolorized with charcoal and evaporated to dryness. The residue is crystallized from methanol-ether to give 1-[2-(4-methyl-2-imidazolylmethyl)phenylcarbamoyl]-4-methylpiperazine, m.p. 177°–179°.

EXAMPLE 14

To a solution of 5 g of 5-(4-methyl-1-piperazinyl)-11H-imidazo[2,1-c][1,3]benzodiazepine in 50 ml of methylene chloride is added in portions 3.75 g of m-chloroperbenzoic acid with stirring at 0°. The mixture is then stirred at room temperature overnight and evaporated to dryness. The foamy residue is passed through 100 g of Amberlite IRA-400 ion exchange resin using water as eluent. Evaporation of the eluent gives 5-(4-methyl-4-oxido-1-piperazinyl)-11H-imidazo[1,2-c][1,3]benzodiazepine as foamy material having Rf=0.173 on silica gel plates using methylene chloride-methanol-ammonium hydroxide (150:50:1) as eluant.

EXAMPLE 15

A mixture of 8.67 g of 5-methylthio-11H-imidazo[2,1-c][1,3]benzodiazepine, 3.38 g of piperazine and 326 ml of amyl alcohol is refluxed under nitrogen for 6 days and evaporated to dryness under reduced pressure. The residue is dissolved in methylene chloride and the solution is washed successively with 10% aqueous potassium carbonate and brine, dried over magnesium sulfate, decolorized with charcoal and evaporated. The residue is chromatographed with 300 g of silica gel using methylene chloride-methanol-ammonium hydroxide (150:50:1) as eluant to give 5-(5H-1-piperazinyl)-11H-imidazo[1,2-c][1,3]benzodiazepine as an oil. The oil is treated with 2.74 g of maleic acid in acetone to give 5-(4H-1-piperazinyl)-11H-imidazo[1,2-c][1,3]benzodiazepine bis-maleate, m.p. 171.5°–173.5°.

EXAMPLE 16

A mixture of 0.2 g of 5-(4-ethoxycarbonyl-1-piperazinyl)-11H-imidazol[1,2-c][1,3]benzodiazepine, 10 ml of tetrahydrofuran and 50 mg of lithium aluminum hydride is refluxed overnight with stirring. The mixture is cooled to 0°, and the excess of the lithium aluminum hydride is destroyed with ethyl acetate, and the mixture is then poured into water and extracted with ethyl acetate. The extracts are dried and evaporated to give after purification 5-(4-methyl-1-piperazinyl)-11H-imidazol[1,2-c][1,3]benzodiazepine of example 1.

EXAMPLE 17

A mixture of 0.1 g of 5-(4H-1-piperazinyl)-11H-imidazo[1,2-c][1,3]benzodiazepine, 0.058 g of methyl iodide, 0.16 g of potassium carbonate and 1 ml of dimethyl-formamide is stirred at room temperature overnight. The mixture is poured into water and extracted three times with ethyl acetate. The extracts are washed with brine, dried and evaporated to give 5-(4-methyl-1-piperazinyl)-11H-imidazo[1,2-c][1,3]benzodiazepine of example 1.

What is claimed is:

1. A compound of the formula

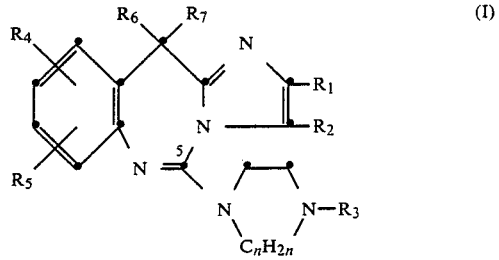

(I)

wherein each of $R_1$ and $R_2$ are hydrogen, lower alkyl, cyano, carboxy, lower alkoxycarbonyl or carbamoyl; n represents the integer 3; $R_3$ is hydrogen, lower alkyl, lower alkoxycarbonyl or hydroxy lower alkyl of 2 to 4 carbon atoms; $R_4$ represents hydrogen, lower alkyl, lower alkoxy, lower alkylthio, halogen or trifluoromethyl; $R_5$ represents hydrogen; and $R_6$ and $R_7$ represent hydrogen or lower alkyl; and N-oxide; or a pharmaceutically acceptable salt thereof.

2. 5-(4-methyl-1-homopiperazinyl)-11H-imidazo[1,2-c][1,3]benzodiazepine.

* * * * *